US00PP22687P2

(12) United States Plant Patent
Lesch

(10) Patent No.: US PP22,687 P2
(45) Date of Patent: Apr. 24, 2012

(54) ***BRUNNERA* PLANT NAMED 'SLDG'**

(50) Latin Name: *Brunnera macrophylla*
Varietal Denomination: SLDG

(76) Inventor: Stephen Sylvester Lesch, Madison, WI (US)

( * ) Notice: Subject to any disclaimer, the term of this patent is extended or adjusted under 35 U.S.C. 154(b) by 0 days.

(21) Appl. No.: 12/931,533

(22) Filed: Feb. 2, 2011

(51) Int. Cl.
*A01H 5/00* (2006.01)

(52) U.S. Cl. ..... Plt./412

(58) Field of Classification Search ..... Plt./412
See application file for complete search history.

*Primary Examiner* — Annette Para
(74) *Attorney, Agent, or Firm* — Klarquist Sparkman, LLP

(57) ABSTRACT

A new and distinct form of *Brunnera macrophylla*, with attractive leaves of yellow green.

1 Drawing Sheet

Botanical denomination: *Brunnera macrophylla.*
Variety designation: 'SLDG'.

BACKGROUND OF THE INVENTION

The present invention relates to a new and distinct cultivar of *Brunnera macrophylla*, given the name, 'SLDG'. *Brunnera* is in the family *Boraginaceae*. This new cultivar was found by the inventor in a garden in Oregon, Wis.

This plant is unique in its foliage coloration. There are no other *Brunnera* on the market with all yellow green foliage.

The new variety has been reproduced only by asexual propagation (division and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a one-year-old *Brunnera* 'SLDG' growing in a one gallon container in flower in the spring in Canby, Oreg.

DETAILED PLANT DESCRIPTION

The following is a detailed description of the new *Brunnera* cultivar based on observations of a one-year-old specimen grown in an unheated shade house in Canby, Oreg. The color descriptions are all based on The Royal Horticultural Society Colour Chart.

Plant:
- *Form.*—Rhizomatous, herbaceous perennial.
- *Cold hardiness.*—USDA Zone 3-8.
- *Size.*—Grows to 60 cm wide and 30 cm high.
- *Vigor.*—Excellent.
- *Stem.*—Rosette.

Leaf:
- *Type.*—Simple.
- *Arrangement.*—Basal.
- *Shape.*—Cordate to ovate.

- *Venation.*—Pinnate.
- *Margins.*—Entire.
- *Apex.*—Acute.
- *Base.*—Cordate.
- *Blade size.*—Grows to 8 cm long and 8 cm wide.
- *Surface texture.*—Coarsely pubescent on both sides.
- *Petiole description.*—Grows to 12 cm long and 2 mm wide, coarsely pubescent, Yellow Green 145A.
- *Leaf color.*—Both sides Yellow Green 145A darkening to Yellow Green 144A in lower light and lightening to Yellow Green 151A interveinally in higher light.

Inflorescence:
- *Type.*—Terminal panicle.
- *Number of flowers.*—100 per panicle.
- *Peduncle.*—21 cm tall and 2 mm wide, pubescent, Yellow Green 145A, with about 9 small petiolate to sessile leaves, grows to 32 mm long and 2.1 mm wide, ovate, entire, acute, attenuate, pubescent with leaf color the same as above.
- *Pedicel.*—3 mm long, less than 1 mm wide, pubescent, Yellow Green 145A.
- *Bloom period.*—May to June in Canby, Oreg.

Flower bud:
- *Size.*—1.3 mm wide and 1.4 mm deep.
- *Description.*—Orbicular.
- *Surface texture.*—Glabrous.
- *Color.*—Purple 76A.

Flower:
- *Type.*—Regular.
- *Shape.*—Rotate.
- *Corolla description.*—5 cm wide and 2 mm deep, top side colored Violet Blue 98A with a White 155D eye, bottom side Violet Blue 97A to 97B; with 5 broadly obovate lobes, each 2 mm wide and 2 mm deep, obtuse, entire, glabrous; tube 1 mm long and 1 to 2 mm wide, outside Purple 77B near lobes to Yellow White 158D.
- *Calyx description.*—Campanulate, 1 mm wide and 1 mm deep, 5-lobed, lobes ovate, acute, entire, pubescent outside, glabrous inside.
- *Pistil description.*—1, 1 mm long, Yellow Green 144A, ovary 4 lobed and about 0.5 mm long, style and stigma 0.5 mm long.

*Stamen description.*—5, filaments 1 mm long and White 155D, anthers 1 mm long and Black 202A, pollen White 155A.

*Fragrance.*—None.

*Lastingness.*—A spike blooms for about 3 weeks on the plant.

Seed: Nutlets, round, less than 1 mm in size, Brown 200A.

Pests and diseases: *Brunnera* have no major pests or disease problems. This plant has shown no special disease or pest resistance in Canby, Oreg.

Comparisons: Compared to the species, *Brunnera macrophylla*, the new variety has yellow green leaves rather than deep green. The yellow green color is held through most of the summer making it a glowing spot in a shade garden or container.

I claim:

1. A new and distinct form of *Brunnera* plant substantially as shown and described.

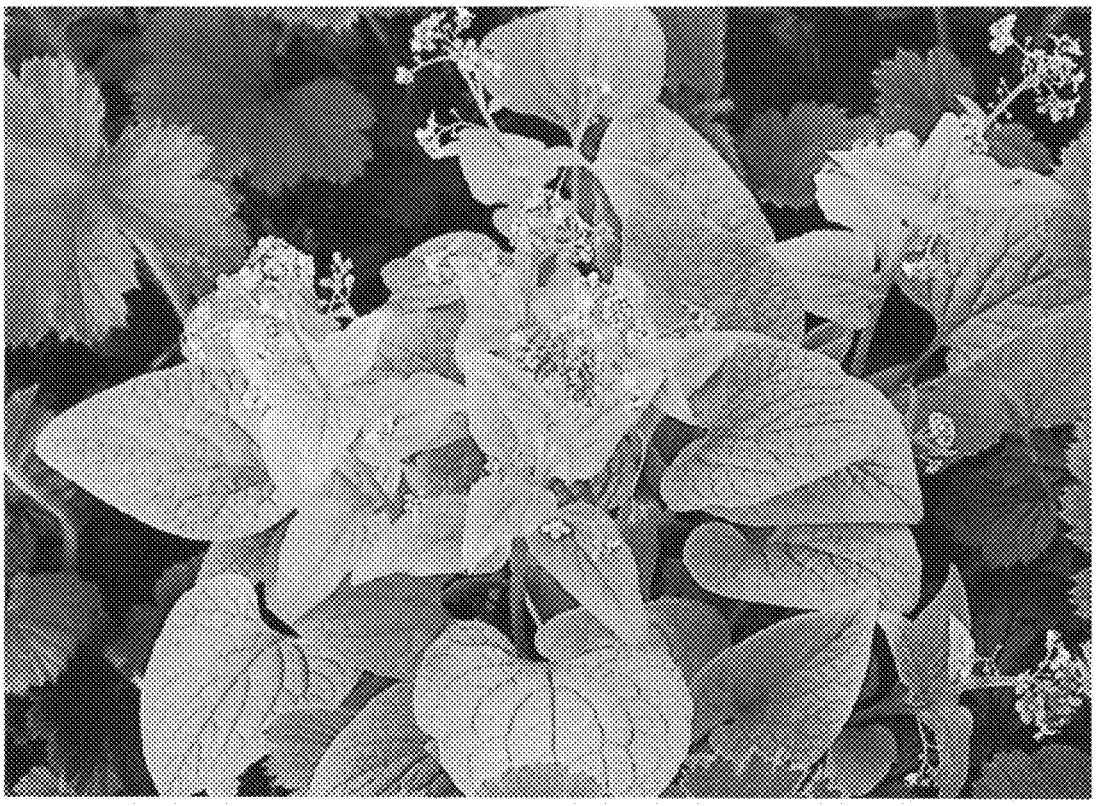

* * * * *